(12) United States Patent
Laine et al.

(10) Patent No.: US 8,410,262 B2
(45) Date of Patent: Apr. 2, 2013

(54) PROCESS FOR THE PREPARATION OF HYDROXY POLYMER ESTERS AND THEIR USE

(75) Inventors: Aki Laine, Raisio (FI); Hendrik Luttikhedde, Markelo (NL)

(73) Assignee: Chemigate Oy, Mietoinen (FI)

( * ) Notice: Subject to any disclaimer, the term of this patent is extended or adjusted under 35 U.S.C. 154(b) by 677 days.

(21) Appl. No.: 12/085,384

(22) PCT Filed: Dec. 7, 2006

(86) PCT No.: PCT/EP2006/011767
§ 371 (c)(1),
(2), (4) Date: May 22, 2008

(87) PCT Pub. No.: WO2007/065681
PCT Pub. Date: Jun. 14, 2007

(65) Prior Publication Data
US 2009/0270606 A1 Oct. 29, 2009

(30) Foreign Application Priority Data
Dec. 8, 2005 (EP) .................................... 05026787

(51) Int. Cl.
*C07H 1/00* (2006.01)
*C08B 31/04* (2006.01)
*C08B 37/00* (2006.01)

(52) U.S. Cl. ......................... 536/124; 536/110; 536/114

(58) Field of Classification Search .................. 536/110, 536/114, 124
See application file for complete search history.

(56) References Cited

U.S. PATENT DOCUMENTS

| 2,170,272 | A |   | 8/1939  | Walsh et al.    |          |
|-----------|---|---|---------|-----------------|----------|
| 2,865,762 | A |   | 12/1958 | Neukom          |          |
| 2,884,412 | A |   | 4/1959  | Neukom          |          |
| 3,499,886 | A |   | 3/1970  | Mehltretter     |          |
| 3,511,830 | A |   | 5/1970  | Speakman        |          |
| 3,513,156 | A |   | 5/1970  | Speakman        |          |
| 3,620,913 | A |   | 11/1971 | Parmerter       |          |
| 4,231,803 | A | * | 11/1980 | Bovier et al.   | 106/162.1|
| 4,958,011 | A | * | 9/1990  | Bade            | 536/20   |
| 5,447,643 | A |   | 9/1995  | Kelkenberg et al.|         |
| 6,365,002 | B1|   | 4/2002  | Bindzus et al.  |          |
| 6,365,140 | B1|   | 4/2002  | Melby et al.    |          |
| 7,091,221 | B2|   | 8/2006  | Kurauchi et al. | 514/336  |
| 2003/0027733 | A1 | | 2/2003 | Kurauchi et al. |          |
| 2007/0009464 | A1 | | 1/2007 | Laine et al.    | 424/70.11|
| 2007/0178125 | A1 | | 8/2007 | Laine et al.    | 424/401  |

FOREIGN PATENT DOCUMENTS

| DE | 4208946           |   | 9/1993  |
|----|-------------------|---|---------|
| EP | 1 270 598         |   | 1/2003  |
| EP | 1270598           | * | 1/2003  |
| FR | 2805270 A1        |   | 8/2001  |
| GB | 1190000           | * | 4/1970  |
| NL | 6717509 A         |   | 7/1968  |
| WO | WO-00/15669 A1    |   | 3/2000  |
| WO | WO-00/50493 A1    |   | 8/2000  |
| WO | WO-02/07684 A1    |   | 1/2002  |
| WO | WO 2004/104049 A1 | * | 2/2004  |
| WO | WO-2004/041732 A1 |   | 5/2004  |
| WO | 2004/104048       |   | 12/2004 |
| WO | 2004/104049       |   | 12/2004 |

OTHER PUBLICATIONS

Greene et al, Protective Groups in Organic Synthesis, 3rd Ed., John Wiley, 1999, pp. 384-385.*
Petrucci et al, General Chemistry, Prentice Hall, 7th Ed., 1997, pp. 592-593.*
Mehltretter et al., "Preparation of Cationic Dialdehyde Starches for Wet-Strength Paper," Tappi, vol. 45, No. 9, 1962, pp. 750-752.
Wing, "Starch Citrate: Preparation and Ion Exchange Properties," Starch/Stärke, vol. 48, Nr. 7/8, 1996, pp. 275-279.

* cited by examiner

*Primary Examiner* — Layla Bland
*Assistant Examiner* — Ganapathy Krishnan
(74) *Attorney, Agent, or Firm* — Drinker Biddle & Reath

(57) ABSTRACT

This invention covers a novel method for the preparation of hydroxy polymer esters of amino, alkylamino and quaternary ammonium acids and their use in several fields of industry, including the use as additives in the manufacture of paper or paperboard. The esterification of the hydroxy polymer, preferably starch, is performed under semianhydrous conditions by heating homogenized mixtures of the hydroxy polymer and reagents.

9 Claims, No Drawings

PROCESS FOR THE PREPARATION OF HYDROXY POLYMER ESTERS AND THEIR USE

This application is the National Stage of International Application No. PCT/EP2006/011767, filed Dec. 7, 2006, which claims priority to EP 05026787.1, filed Dec. 8, 2005.

SUMMARY OF THE INVENTION

This invention covers a novel method for the preparation of hydroxy polymer esters of amino, alkylamino and quaternary ammonium acids and their use in several fields of industry, including the use as additives in the manufacture of paper or paperboard, food products, water treatment, textiles and cosmetics. The trans esterification of the hydroxy polymer, preferably starch, is performed under anhydrous or semianhydrous conditions by heating homogenised mixtures of a hydroxy polymer and an amino, alkylamino or quaternary ammonium acid ester in the presence of alkalising agent. The process is especially suitable for the feasible production of cationic starch esters of natural cationic carboxylic acids such as betaine and carnitine.

BACKGROUND OF THE INVENTION

Chemically modified amino and ammonium functional hydroxy polymers, especially carbohydrates, are widely used in industrial applications from building materials and paper production to pharmaceuticals and cosmetics. Starch is one of the most important natural hydroxy polymers. It is a renewable and feasible raw material and the third most used component by weight in paper industry, where the main role of starch is to improve the strength of the paper. Starch is also used as an adhesive in surface sizing and as a binder in coating formulations. The bonding of starch to cellulosic fibres is generally improved by addition of cationic substituents to the starch backbone. The positively charged cationic starch, containing amino or ammonium groups, has a strong affinity for negatively charged surfaces and particles i.e. cellulosic fibres and mineral pigments.

Cationic starches are also used in textile industry to improve the textile feel of the fabric. In U.S. Pat. No. 5,447,643 an aqueous fabric softener is stabilised by addition of cationic starch or chitosan.

In waste water treatment, the use of cationic starches improves the retention of anionic impurities in the flocculation processes. For instance, patent publication WO 2004/041732 introduces the use of cationic starch and a brine solution in the treatment of water and wastewater.

Cationic hydroxy polymers have also a strong affinity for keratinous matter and therefore cationized guar gum and starch are widely used in hair and skin care products. The use of low molecular weight cationic starches in cosmetics and the treatment of a keratin-containing substrate is disclosed in U.S. Pat. No. 6,365,140. Another cosmetic treatment composition comprising cationic starch betainate has been described in patent publication WO 02/07684, which also covers a cosmetic treatment method for keratinous matter and use for washing skin.

Several methods have been developed for the cationization of starch and other hydroxy polymers. The cationization is generally carried out by etherification of starch with 2,3-epoxypropyl trimethylammonium chloride or 3-chloro-2-hydroxypropyl trimethylammonium chloride in an alkaline aqueous slurry or a dry process. The common cationization reagent can give undesirable reaction by-products.

The generally known methods for preparing carboxylic acid esters of starch involve the use of acid chlorides or anhydrides in organic solvents such as pyridine or 1,4-dioxane. Patent publication WO 00/15669 illustrates the esterification of starch using acid chloride of betaine in 1,4-dioxane and pyridine. Patent FR 2805270 concerns novel types of cationic polymers and polymeric matrices, degradable in the organism, and with controlled rate of degradation, useful as such or as vehicles for different compounds, in particular molecules with biological activity. FR 2805270 also describes a method for producing said polymers and matrices from maltodextrins and acid chlorides of betaines in pyridine and DMF.

The use of undesired and relatively expensive solvents and reagents generate both environmental load and high price for starch esters and may leave traces of harmful substances in final products. Therefore, the general esterification methods do not fulfil the requirements for the large-volume and low-cost starch esters, especially when the application of the starch ester may be involved in food products, cosmetics or pharmaceuticals.

A method for the preparation of phosphate esters of starch by heating dry mixtures of starch and inorganic salts of phosphoric acid is generally known. The common manufacturing procedures are exemplified by U.S. Pat. No. 2,884,412 and U.S. Pat. No. 2,865,762. These procedures involve impregnating starch granules with alkali metal phosphates or other phosphate reagents in aqueous slurries, drying of the starch granules without gelatinizing them to a moisture content of less than 20%, and then heating of the dry granules to reaction temperatures of about 120 to 175° C. A similar dry phosphorylation process is described in U.S. Pat. No. 6,365,002, where amphoteric starch additives for papermaking are produced by phosphorylation of cationic starch. The amphoteric starch phosphates provide advantageous paper properties and improved wet end performance.

An analogous method for the preparation of highly crosslinked and water insoluble starch esters of citric acid has been published in Starch/Stärke 48 (1996) 275-279. In the esterification procedure, dry mixtures of starch and sodium salts of citric acid are heated at 110-140° C. for 2-24 h. The thus prepared water-insoluble starch citrates were used as biodegradable ion-exchangers for metal ions.

In the patent publication DE 4208946, water insoluble starch acetates containing amino acid esters are prepared for the manufacture of biodegradable plastics. However, the procedure involves the use of acid anhydrides, and produces amino acid esters in N-acylated form. The N-acylation of amino acids is usually an undesired reaction and reduces the functionality of amino acid esters of starch in applications where the presence of free amino groups is required.

The production of anthranilic acid ester of starch and its use as a paper retention aid has been described in the patents NL 6717509, U.S. Pat. No. 3,499,886, U.S. Pat. No. 3,511,830, U.S. Pat. No. 3,513,156 and U.S. Pat. No. 3,620,913. The esterification of starch is performed using isatoic anhydride in an organic solvent or an aqueous slurry. Isatoic anhydride (i.e. N-carboxy anhydride of anthranilic acid) is generally prepared from anthranilic acid and phosgene. The hydrolysis product shows biological activity.

A retention aid for chemical pulp prepared by derivatization of dialdehyde starch with betaine hydrazide has been described in Tappi 44 (1962) 750. However, the thus formed hydrazones of starch are harmful and their preparation is complex and unfeasible.

U.S. Pat. No. 2,170,272 describes the thinning of starch pastes for textile and paper sizing purposes by heating starch pastes in the presence of acid salts of amino acids, such as betaine hydrochloride. The thinning process is carried out for starch pastes containing over 90% of water at temperatures around 85° C. and therefore, no esterification of amino acids is involved. The purpose of amino acids in the patented process is to immobilise strong acids, which are responsible for the thinning (i.e. acid hydrolysis) of starch, so that dry blends of acid salts and starch can be safely stored prior to the thinning by cooking.

Patent publication WO 2004/104049 covers a method for the preparation of carnitine esters of starch and other hydroxy polymers, and their use in several fields of industry, for example as an additive in the manufacture of paper. The esterification of a hydroxy polymer, preferably starch, with β-lactone of carnitine is most feasibly carried out in an aqueous slurry. The carnitine esters of starch are considered as more physiologically acceptable and biodegradable than traditional cationic starch ethers.

Patent publication US 2003/0027733 describes the preparation of nitrogenous carboxylic esters of cellulose to be used as antibacterial agents with flame retardant properties. The invented process consists of a heat-treatment of cellulose in the presence of certain amino acid esters. However, the process has a very poor reaction efficiency of 1-10% and the harsh and highly acidic reaction conditions exploiting hydrochlorides of amino acids are not suitable for more sensitive hydroxy polymers i.e. starch.

Patent publication WO 2004/104048 describes a solventless esterification process of starch and other hydroxy polymers, where the homogenous mixtures of a hydroxy polymer, a free amino, alkylamino or quaternary ammonium acid and an acidulating agent are heated to yield hydroxy polymer esters containing amino, alkylamino or quaternary ammonium groups. The invented process simultaneously hydrolyses the polymer structure during the esterification in acidic conditions, which may restrict the available molecular weight range of the products.

Patent publication WO 00/50493 concerns a method for making a cellulose or starch fatty ester by esterification or trans esterification of a cellulosic or starchy material using a fatty reagent. The process is performed in solid or fragmented state in a double screw extruder at a temperature ranging between 180° C. and 230° C. The invented method claims to make cellulosic or starchy material hydrophobic without using toxic solvents.

The new process improves the former dry esterification process described in the patent publication WO 2004/104048 by introducing the use of esters of amino, alkylamino and quaternary ammonium acids, preferably methyl betainate chloride and methyl carnitate chloride as esterifying agents. The new alkaline trans esterification process allows far greater reaction efficiencies (RE) and much better preservation of high molecular weights of hydroxypolymer than the former acidic dry esterification process of nitrogenous carboxylic acids. Hereby, the use of alkalising agent, such as ammonia, to promote solid state trans esterification allows the production amino or quaternary ammonium functional hydroxy polymer esters with a reasonable yield and only negligible decrease in the molecular weight.

DETAILED DESCRIPTION OF THE INVENTION

This invention covers a novel method for preparation of amino, alkylamino and quaternary ammonium acid esters of starch and other hydroxy polymers. These esters can replace conventional cationic polymers in numerous applications. The invented process is especially suitable for the production of cationic esters of high molecular weight starch. The process does not include undesired substances, and the starch esters prepared according to the invention are more biodegradable than for example the traditional cationic starch ethers.

In this invention, a hydroxy polymer, preferably starch, and a natural or a synthetic, amino, alkylamino or quaternary ammonium acid ester are trans esterified in a dry process without additional solvents. An alkalising agent is used to promote the esterification and to protect high molecular weight hydroxypolymers from hydrolysis.

A preferred hydroxy polymer for the invented process is unmodified granular starch, although modified starches can be used as well. However, other hydroxy functional polymers such as modified or unmodified cellulose, chitosan, guar gum, xanthan, pullulan, polyvinyl alcohol and mixtures thereof are also applicable.

The quaternary ammonium acid ester is preferably selected from the group consisting of C1-C8 alkyl esters of betaine, propiobetaine, butyrobetaine, crotonobetaine, valerobetaine, 2-betainyllactate, carnitine, acetylcarnitine, dehydrocarnitine, succinylmonocholine and mixtures thereof. Methyl and ethyl esters of betaine and carnitine are preferred. The amino and alkylamino esters are preferably selected from the group consisting of C1-C8 alkyl esters of glycine, alanine, leucine, serine, threonine, tyrosine, valine, phenylalanine, cysteine, asparagine, aspartic acid, glutamic acid, methionine, lysine, proline and mixtures thereof. These do not however exclude the use of other similar nitrogenous carboxylic acid esters as raw materials.

The alkalising agent is preferably an inorganic or organic base selected from the group consisting of $NaHCO_3$, $K_2CO_3$, NaOH, KOH, ammonia, trimethylamine, triethylamine, pyridine, dimethylaminopyridine, DABCO (1,4-diazabicyclo[2.2.2]octane) and mixtures thereof, but this group does not however exclude the use of other similar bases. Gaseous alkalising agents such as ammonia are highly preferred as they readily penetrate into the dry reaction mixtures of the hydroxy polymers and the nitrogenous carboxylic esters. In addition, gaseous alkalising agents are easily evaporated after the esterification process, which reduces the risk of alkaline hydrolysis of the hydroxy polymer esters afterwards. The alkali lability of esters should be taken into account especially in the production of betaine esters, which are more alkali labile than conventional carboxylic acid esters. Therefore, all the aqueous processing and prolonged storing of the hydroxy polymer esters should be concluded in the acidic or neutral pH range. In particular cases, it is advantageous to use alkali liberating compounds such as urea, ammonium carbamate, methyl carbamate, urethane, ammonium bicarbonate, ammonium formate, ammonium oxalate, ammonium citrate and mixtures thereof as alkalising agents. Urea is especially preferred as it liberates catalytic amounts of ammonia upon heating to promote the trans esterification and also simultaneously renders carbamate groups on the hydroxypolymers.

In the preferred trans esterification method according to this invention, a hydroxy polymer is mixed with an amino, alkylamino and quaternary ammonium acid ester. Small amounts of water can be used to impregnate the hydroxy polymer with the esterifying reagents. An alkalising agent may also be mixed to the moist mixture or it can be introduced later on. To reduce the risk of alkaline hydrolysis, the alkalising agent is preferably added only after a vigorous drying of the reaction mixture of the hydroxy polymer and the nitrogenous carboxylic ester. The drying of the reaction mixture should be performed at mild temperatures to prevent undesired hydrolysis and processability problems. When granular starch is used as a hydroxy polymer, the drying temperature is preferably below the gelatinization temperature of starch. Prior to the esterification, the moisture content of the reaction mixture is preferably less than 25% and more preferably less than 5% of water. The trans esterification reaction is performed by heating the dry and homogeneous mixture of the hydroxy polymer, the nitrogenous carboxylic acid ester and the alkalising agent at 50-230° C., preferably at 80-160° C., e.g. for 1-50 h. The reaction time may vary from minutes to several days and is dependent on the type of the reactor, the reaction temperature and the choice of reagents. The reaction efficiency (RE) of the esterification is typically 20-50% and consecutive reaction steps may be used to improve the RE. Depending on the application, the unreacted reagents may remain in the final product or the hydroxy polymer ester may be purified, e.g. by suspending it in water and precipitating with ethanol, acetone or other appropriate solvent. In the case of granular starch with a low DS (below 0.1), washing of the raw product with water is preferred.

Variable degrees of substitution (DS) may be achieved for the hydroxy polymer esters. The invented process is the most suitable for the production of nitrogenous carboxylic esters having a DS lower than 0.2, but also higher degrees of substitution are possible.

The molecular weight of the final hydroxy polymer ester is strongly dependent on the reaction temperature and time, along with the choice of reagents and the moisture content of the reaction mixture during the heating phase. In certain applications, where low viscosity and high concentration solutions are required, an adequate level of hydrolysis of the hydroxy polymer is preferred. The invented process enables the careful preservation of high molecular weights of the hydroxypolymers, but the process can be adjusted to provide controlled degradation and lower molecular weights as well. For instance, higher reaction temperatures favor the degradation of molecular weights and prolonged heating after the elimination of alkalising agent accelerate this degradation process. This allows the preparation of versatile products with a wide range of molecular weights.

In order to achieve a sufficiently high solids content of starch in the paper manufacture, the conventional cationic starches are usually thinned (i.e. acid hydrolysed or oxidised) prior to the cationization, which adds an additional step and expenses to the process. In the invented process, a simultaneous thinning of starch may occur during the esterification process. Consequently, a separate thinning process of starch is not needed, and unmodified starches may be used as an expedient raw material. This does not however exclude the use of thinned or otherwise modified starch.

The invented process comprises solely of risk-free and economical raw materials, and the products are fully biodegradable. In addition, the trans esterification process has a good reaction efficiency without major degradation of the molecular weight of the hydroxy polymers. The invented process can be feasibly performed using various apparatuses, such as ovens, dryers, microwave reactors, kneaders, fluidised beds, extruders, etc., which allow an easy and economical scale up of the ester production. If desired, the processability of the reaction mixture can be enhanced with suitable plasticizers, such as glycerol, ethylene glycol, diethylene glycol, urea, ethanolamine, diethanolamine, triethanolamine, trimethylolethane, sorbitol, maltitol, sucrose or fructose.

The hydroxy polymer esters produced according to the invented process are suitable for paper manufacture, e.g. as wet end additives and in the paper sizing applications. Due to biodegradability, physiologically acceptable properties, and the avoidance of undesired raw materials, the nitrogenous carboxylic acid esters of hydroxy polymers are applicable especially as additives of food, paper or paperboard, and in effluent treatment, cosmetics and pharmaceutics.

It will be appreciated that the essence of the present invention can be incorporated in the form of variety of embodiments, only a few of which are disclosed herein. It will be apparent for the skilled person that other embodiments exist and do not depart from the spirit of the invention. Thus the described embodiments should not be construed as restrictive. For example although starch and betaine esters are the most preferred raw materials for the process, also numerous other hydroxy polymers and nitrogenous carboxylic acid esters may be used instead.

EXAMPLES

Comparative Example 1

In Neutral Conditions

Methyl betainate chloride (2.07 g; 0.20 mol equiv.) was dissolved in 10 ml of water and mixed with native potato starch (10.0 g; 1.0 mol equiv.). Water was evaporated at reduced pressure and the dry mixture was heated in an oven at 140° C. for 6 h. The neutral reaction mixture became gradually acidic during the heating process, which weakly promoted the esterification of starch, but also reduced the molecular weight of the starch betainate. The starch ester characterised with $^1$H NMR had the betainate DS of 0.01 (RE 5%). According to the size exclusion chromatography the weight-average molecular weight of the starch ester was 410 000 daltons.

Esterification of starch with methyl betainate chloride yielded a very poor RE and the MW of the starch ester was quite low.

Comparative Example 2

With an Acidulating Agent

Methyl betainate chloride (19.9 g; 0.32 mol equiv.) and DL-lactic acid (9.3 g; 0.28 mol equiv.) were dissolved in 80 ml of water. The solution was mixed with dry native potato starch (60.0 g; 1.0 mol equiv.). The mixture was carefully dried in a rotavapor. The dry mixture was heated in an oven at 140° C. for 7 h. The raw product was purified by slurrying it in 150 ml of water, precipitating with 300 ml of ethanol and filtering. The dried starch ester characterised with $^1$H NMR had the betainate DS of 0.09 (RE 28%) and the lactate DS of 0.13 (RE 46%). According to the size exclusion chromatography the weight-average molecular weight of the product was 83 000 daltons. Esterification of starch with methyl betainate chloride and DL-lactic acid yielded a better RE, but the molecular weight of the starch ester was highly degraded.

Example 1

Ammonia Assisted Esterification of Starch with Methyl Betainate Chloride

Methyl betainate chloride (9.3 g; 0.15 mol equiv.) was dissolved in 60 ml of water and mixed with native potato starch (60.0 g; 1.0 mol equiv.). The mixture was carefully dried in a rotavapor. The esterification was performed in a heated flask with an unheated phase separator and a capillary exit to the atmosphere. The flask was heated at 140° C. in an oil bath and 5 ml of 7 M ammonia in methanol was injected via septum. After heating for 5 h, ammonia was evaporated. The unreacted methyl betainate and free betaine were removed by slurrying the raw product in water, precipitating with ethanol and filtrating. The dried starch ester characterised with $^1$H NMR had the betainate DS of 0.038 (RE 27%). According to the size exclusion chromatography the weight-average molecular weight of the starch betainate was 4 600 000 daltons.

Example 2

Ammonia Assisted Esterification of Starch with Methyl Betainate Chloride

Methyl betainate chloride (18.6 g; 0.60 mol equiv.) was dissolved in 60 ml of water and mixed with native potato starch (30.0 g; 1.0 mol equiv.). The mixture was carefully dried in a rotavapor. The cationization was performed in a heated flask with an unheated phase separator and a capillary exit to the atmosphere. The unstirred mixture was heated at 130° C. in an oil bath and 5 ml of 7 M ammonia in methanol was injected via septum. After heating for 22 h, ammonia was evaporated. The unreacted methyl betainate and free betaine were removed by slurrying the raw product in water, precipitating with ethanol and filtrating. The dried starch ester characterised with $^1$H NMR had the betainate DS of 0.13 (RE 22%). According to the size exclusion chromatography the weight-average molecular weight of the product was 9 700 000 daltons.

Example 3

Ammonia Assisted Esterification of Starch with Methyl Betainate Chloride

Methyl betainate chloride (680 g, 0.12 mol equiv.) was dissolved in 400 ml of water and sprayed into vigorously mixed native potato starch (5500 g; 1.0 mol equiv.) in the Lödige VT50 contact dryer. The spraying equipment was rinsed with 100 ml of water and the reaction mixture was dried at reduced pressure at temperatures up to 90° C. 7 M ammonia in methanol (160 ml) was injected and the heating of the reactor's jacket with 130° C. steam was started. After 2 hours, 7 M ammonia in methanol (40 ml) was injected and the reaction was resumed for another 2 hours. After total reaction time of 4 hours at a reaction temperature of around 110° C., the residues of ammonia and methanol were removed at reduced pressure. A water washed sample of the raw product characterised with $^1$H NMR had the betainate DS of 0.029 (RE 24%). According to the size exclusion chromatography the weight-average molecular weight of the product was 1 200 000 daltons.

Example 4

Urea Assisted Esterification of Starch with Methyl Betainate Chloride

Methyl betainate chloride (11.7 g, 0.20 mol equiv.) and urea (22.9 g, 1.0 mol equiv.) were dissolved in 30 ml of water and mixed with native potato starch (50.0 g, 1.0 mol equiv.). The mixture was dried at reduced pressure at 50-90° C. for 6 h. The dry reaction mixture was heated in a closed flask with a capillary exit at 130° C. for 3.5 h. The presence of ammonia was confirmed as a moist pH paper displayed pH 10-11 in the atmosphere of the reaction vessel. After evaporation of ammonia, the raw product was purified twice by slurrying in water, precipitating with ethanol and filtrating. The dried starch ester characterised with $^1$H NMR had the betainate DS of 0.09 (RE 45%).

Example 5

Ammonia Assisted Esterification of Starch with Methyl Carnitate Chloride

Methyl carnitate chloride (10.2 g; 0.13 mol equiv.) was dissolved in 60 ml of water and mixed with native potato starch (60.0 g; 1.0 mol equiv.). The mixture was carefully dried in a rotavapor. The cationization was performed in a heated flask with an unheated phase separator and a capillary exit to the atmosphere. The unstirred mixture was heated at 140° C. in an oil bath and 0.5 ml of 7 M ammonia in methanol was injected via septum. After heating for 6 h, ammonia was evaporated. The unreacted methyl carnitate and free carnitine were washed from the raw product with water. The dried starch ester characterised with $^1$H NMR had the carnitate DS of 0.032 (RE 25%). According to the size exclusion chromatography the weight-average molecular weight of the product was 7 900 000 daltons.

Example 6

Ammonia Assisted Esterification of Starch with Methyl Carnitate Chloride

Methyl carnitate chloride (15.7 g; 0.20 mol equiv.) was dissolved in 60 ml of water and mixed with native potato starch (60.0 g; 1.0 mol equiv.). The mixture was carefully dried in a rotavapor. The cationization was performed in a heated flask with an unheated phase separator and a capillary exit to the atmosphere. The dry mixture was heated at 130° C. in an oil bath and 5 ml of 7 M ammonia in methanol was injected via septum. After heating for 15.5 h, ammonia was removed in vacuum. The unreacted methyl carnitate and free carnitine were removed by slurrying the raw product twice in water, precipitating with ethanol and filtrating. The final product was dried in a vacuum oven overnight at 65° C. The dried starch ester characterised with $^1$H NMR had the carnitate DS of 0.06 (RE 30%).

Example 7

Ammonia Assisted Esterification of Guar Gum with Methyl Betainate Chloride

Methyl betainate chloride (4.14 g; 0.20 mol equiv.) was dissolved in 400 ml of water and mixed with guar gum (20.0 g; 1.0 mol equiv.). The mixture was carefully dried in a vacuum oven. The cationization was performed in a heated flask with an unheated phase separator and a capillary exit to the atmosphere. The mixture was heated at 120° C. in an oil bath and 3 ml of 7 M ammonia in methanol was injected via septum. After heating for 42 h at 120° C., ammonia was removed in vacuum. The raw product was purified by dissolving in water and precipitating with ethanol. The dried guar gum betainate characterised with $^1$H NMR had the betainate DS of 0.02 (RE 10%).

Example 8

Ammonia Assisted Esterification of Starch with L-leucine Methyl Ester

L-leucine methyl ester hydrochloride (4.49 g; 0.20 mol equiv.) was dissolved in 30 ml of water and mixed with native potato starch (20.0 g; 1.0 mol equiv.). The mixture was carefully dried in a rotavapor. The cationization was performed in a heated flask with an unheated phase separator and a capillary exit to the atmosphere. The unstirred mixture was heated at 120° C. in an oil bath and 4 ml of 7 M ammonia in methanol was injected via septum. After heating for 17 h, ammonia was evaporated. The unreacted L-leucines were removed by slurrying the raw product in water, precipitating with ethanol and filtrating. The dried starch ester characterised with $^1$H NMR had the L-leucinate DS of 0.04 (RE 20%).

Example 9

Ammonia Assisted Esterification of Starch with L-proline Methyl Ester

L-proline methyl ester hydrochloride (4.02 g; 0.20 mol equiv.) was dissolved in 30 ml of water and mixed with native potato starch (20.0 g; 1.0 mol equiv.). The mixture was carefully dried in a rotavapor. The cationization was performed in a heated flask with an unheated phase separator and a capillary exit to the atmosphere. The unstirred mixture was heated at 110° C. in an oil bath and 3 ml of 7 M ammonia in methanol was injected via septum. After heating for 15 h, ammonia was evaporated. The unreacted L-prolines were removed by slurrying the raw product in water, precipitating with ethanol and filtrating. The dried starch ester characterised with $^1$H NMR had the L-prolinate DS of 0.02 (RE 10%).

The invention claimed is:

1. A process for the preparation of a hydroxy polymer ester containing an amino, alkylamino, or quaternary ammonium group comprising:
   mixing a hydroxy polymer with an amino, alkylamino, or quaternary ammonium acid ester to produce a reaction mixture;
   drying the reaction mixture to produce a dry reaction mixture, wherein the dry reaction mixture has a moisture content of less than 10% water;
   adding an alkalising agent to the dry reaction mixture after the drying step, wherein the alkalising agent is ammonia or urea; and
   heating the dry reaction mixture and the alkalising agent to a temperature range of 50-230° C.

2. The process according to claim 1, characterised in that the amino, alkylamino or quaternary ammonium acid ester contains at least one carboxylic acid ester group and at least one primary, secondary or tertiary amino or quaternary ammonium group.

3. The process according to claim 1, characterised in that the amino, alkylamino or quaternary ammonium acid ester is a C1-C8 alkyl ester.

4. The process according to claim 1, characterised in that the amino, alkylamino or quaternary ammonium acid ester is selected from the group consisting of methyl and ethyl esters of betaine, propiobetaine, butyrobetaine, crotonobetaine, valerobetaine, 2-betainyllactate, carnitine, acetylcarnitine, dehydrocarnitine, succinylmonocholine, glycine, alanine, leucine, serine, threonine, tyrosine, valine, phenylalanine, cysteine, asparagine, aspartic acid, glutamic acid, methionine, lysine, proline and mixtures thereof.

5. The process according to claim 1, characterised in that the hydroxy polymer is selected from the group consisting of unmodified or modified starch, cellulose, chitosan, guar gum, xanthan, pullulan, polyvinyl alcohol and mixtures thereof.

6. The process according to claim 1, characterised in that the reaction mixture contains a plasticizer.

7. The process according to claim 1, characterised in that the amino, alkylamino or quaternary ammonium acid ester is a methyl or ethyl ester.

8. The process according to claim 1, characterised in that the reaction mixture contains a plasticizer selected from the group consisting of glycerol, ethylene glycol, diethylene glycol, ethanolamine, diethanolamine, triethanolamine, trimethylolethane, sorbitol, maltitol, sucrose, fructose and mixtures thereof.

9. A process for the preparation of a hydroxy polymer ester containing an amino, alkylamino or quaternary ammonium group comprising:
   mixing a hydroxy polymer with an amino, alkylamino or quaternary ammonium acid ester to produce a reaction mixture;
   drying the reaction mixture to produce a dry reaction mixture, wherein the dry reaction mixture has a moisture content of less than 10% water;
   adding an alkalising agent to the dry reaction mixture after the drying step, wherein the alkalising agent is ammonia or urea; and
   heating the dry reaction mixture and the alkalising agent to a temperature range of 50-230° C.,
   wherein the amino, alkylamino or quaternary ammonium acid ester is selected from the group consisting of methyl and ethyl esters of betaine, propiobetaine, crotonobetaine, 2-betainyllactate, carnitine, acetylcarnitine, dehydrocarnitine, succinylmonocholine, and mixtures thereof.

* * * * *